United States Patent
Chevet et al.

(10) Patent No.: US 10,272,025 B2
(45) Date of Patent: Apr. 30, 2019

(54) PERFUMING COMPOSITION

(71) Applicant: LVMH RECHERCHE, Saint-Jean de Braye (FR)

(72) Inventors: Karine Chevet, Chateauneuf sur Loire (FR); Valerie Alard, Orleans (FR); Marie-Laure Souvie, Semoy (FR); Brigitte Noe, Orleans (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 15/320,135

(22) PCT Filed: Jun. 29, 2015

(86) PCT No.: PCT/FR2015/051770
§ 371 (c)(1),
(2) Date: Dec. 19, 2016

(87) PCT Pub. No.: WO2016/001560
PCT Pub. Date: Jan. 7, 2016

(65) Prior Publication Data
US 2017/0128347 A1    May 11, 2017

(30) Foreign Application Priority Data

Jun. 30, 2014 (FR) ...................... 1456116

(51) Int. Cl.
*A61K 8/00* (2006.01)
*A61K 8/81* (2006.01)
*A61K 8/34* (2006.01)
*A61Q 13/00* (2006.01)

(52) U.S. Cl.
CPC .............. *A61K 8/8182* (2013.01); *A61K 8/34* (2013.01); *A61Q 13/00* (2013.01)

(58) Field of Classification Search
CPC .................................................. A61K 8/8182
See application file for complete search history.

(56) References Cited

U.S. PATENT DOCUMENTS

| 3,800,033 A | 3/1974 | Flawn et al. |
| 3,939,099 A * | 2/1976 | Tusa ...................... A61K 8/731 512/2 |
| 6,063,365 A * | 5/2000 | Shefer ..................... A61L 9/042 424/65 |
| 2007/0148213 A1* | 6/2007 | Ibrahim ............... A61K 8/0208 424/443 |
| 2010/0267606 A1 | 10/2010 | Tabarie et al. |
| 2012/0097754 A1* | 4/2012 | Vlad ........................ A61L 9/01 239/6 |

FOREIGN PATENT DOCUMENTS

| FR | 2162563 | 8/1977 |
| FR | 2952534 | 5/2011 |

OTHER PUBLICATIONS

Luviskol VA 64 Product Data Sheet. Obtained Apr. 10, 2018 at: https://www.carecreations.basf.com/product-formulations/products/products-detail/LUVISKOL%20VA%2064%20POWDER/30035019 (Year: 2018).*
International Search Report issued in International Application No. PCT/FR2015/051770 dated Sep. 24, 2015 (7 pages).
Written Opinion issued in International Application No. PCT/FR2015/051770 dated Sep. 24, 2015 (6 pages).
Office Action issued for European Patent Application No. 15742359.1, dated Jan. 3, 2019, 7 pages including English translation.

* cited by examiner

*Primary Examiner* — Arrie L Reuther
(74) *Attorney, Agent, or Firm* — Hamre, Schumann, Mueller & Larson, P.C.

(57) ABSTRACT

The present invention relates to a perfuming eau de toilette or eau de parfum composition comprising a high proportion of alcohol, for direct application on the skin or hair by spraying. More specifically, it relates to a sprayable perfume composition having excellent properties such as persistence of the olfactory note once applied on the skin. The composition is transparent and contains ethanol, 0 to 30% by weight of water, 3 to 40% by weight of a perfume concentrate and a copolymer of vinylpyrrolidone and vinyl acetate.

9 Claims, No Drawings

PERFUMING COMPOSITION

The present invention relates to a perfuming composition containing a high proportion of alcohol, intended to be applied by spraying, directly to the skin and the hair or else to clothing.

This composition may be an eau de toilette, an eau de cologne, a perfume extract, an esprit de parfum or an eau de parfum. It is not rinsed off after application.

More specifically, the invention relates to a perfuming composition which has excellent properties such as transparency, sprayability, olfactory fidelity of the perfume concentrate that it contains, and persistence of the perfume note over time after application.

PRIOR ART

A perfume generally contains a perfume concentrate, ethanol, optionally water, and additives such as solubilizing agents, dyes, antioxidants and surfactants.

The perfume concentrate is an essential constituent of the perfume. It essentially contains odorous volatile substances which are combined, so as to give the perfume its original olfactory note.

The development of a perfuming solution involves the selection of the nature and amount of these various ingredients for the purpose of obtaining a liquor in accordance with regulations, having optimal organoleptic characteristics and good stability.

The perfume must in particular exhibit light-stability and heat-stability sufficient to guarantee that the olfactory note is maintained in the packaging during its storage until the product is sold, and then throughout the duration of its use by the consumer. This stability involves mainly the preservation over time of the original olfactory note and the absence of appearance of cloudiness or deposits in the bottle.

The odor of a perfume, also called "olfactory note" in the present application, is the result perceived by the sense of smell of the emanation of the volatile substances that it contains. By adjusting the degree of volatility of the odorous substances, and the thresholds of perception by the sense of smell, a perfume is composed, the olfactory note of which changes over the hours following applications to the skin or the hair.

Thus, each perfume exhibits what is referred to as i) a top note which is the odor that diffuses first during the application of the perfume or during the opening of the container containing it, ii) a heart or body note which corresponds to the complete perfume (emission for a few hours after gradual extinction of the top note) and iii) a base note which is the most persistent odor (emission for several hours after the heart note). The persistence of the base note corresponds to what perfumers call the persistence of the perfume.

For some perfume concentrates, it would be sought to increase the persistence of the olfactory note of the perfuming solution, in order to prolong the consumer's odor perception over time, once the perfuming composition has been applied. It may also be sought to preserve the strength of the more volatile notes, such as the top notes and the heart notes.

In any event, it is essential to incorporate, into the perfuming solutions, compounds which do not modify the scent as a whole, in particular the top, heart and base notes, qualitatively (odor perceived) and quantitatively (strength perceived), in order to guarantee the olfactory fidelity of the perfume concentrate.

Thus, multiple parameters must be adjusted in order to obtain a satisfactory product. However, a given additive may introduce undesirable properties simultaneously with its main function, so that the perfumer may be led to make compromises.

For example, the strength and the persistence of an olfactory note may depend on the nature of the perfume concentrate, on the percentage of the concentrate in the solution, on the level of alcohol and on the maceration time. The color depends on the liquor filtration parameters and also on the addition of dyes. A system for protecting and stabilizing the perfume concentrate comprising antioxidants and sunscreens protecting the perfuming solution against the action of UV radiation may be required in order to limit the deterioration of the liquor in response to light and heat. Furthermore, the toxicological innocuousness of the formula and the good compatibility thereof with the container must be verified.

The main negative feedback from consumers regarding perfuming products such as eaux de toilette are often their lack of persistence on skin: the perception of the odor of the product once applied is judged to be too short, so that the consumer may be obliged to reapply the product one or more times during the day, in order to maintain the perception of its odor over time. Thus, during the preparation of a perfume composition, there may be cause to incorporate therein compounds which delay their evaporation, such as fixers or agents which modify their evaporation curve.

However, some fixers and some modifiers of the evaporation profile have the drawback of modifying the organoleptic properties of an alcoholic solution of the perfume concentrate. They may thus modulate the perfume notes of the perfuming product that are perceived after application of the product to the skin or clothing. They may also leave on the skin a greasy or tacky feel to the touch, or modify the appearance of the solution by substantially reducing its transparency or by increasing its viscosity. Finally, they may reduce the heat-stability and light-stability of the solution.

There therefore remains the need to provide compounds which increase the duration of the perception of the note of the perfume, without modifying the color and the olfactory identity of the perfume concentrate of which it is desired to preserve the notes. These compounds must also make it possible to preserve the transparency of the perfuming solution, be able to be sprayed through a suitable device such as the nozzle of a bottle, and not leave tacky residues on the skin.

The inventors have found a compound of polymer type which corresponds to these complex specifications. This is all the more surprising since many other polymers do not make it possible to satisfy these specifications. This is the case in particular of methacrylate derivatives which have a totally unacceptable odor, cellulose derivatives for which a compromise between the extending effect and the sprayable nature could not be found, and polyvinylpyrrolidones which result in solutions that are too viscous to be sprayed, or in solutions which are sprayable but the extending effect of which is not significant. Finally, other polymers result in perfuming solutions which leave a tacky feeling on the skin.

The inventors have found, surprisingly, that a vinylpyrrolidone/vinyl acetate copolymer makes it possible to preserve and extend the original olfactory note of perfumes while at the same time preserving their sprayable nature. This compound thus makes it possible to extend the odor perception of the materials present in the perfume concentrate, which has been diluted in an alcohol.

Vinylpyrrolidone/vinyl acetate copolymers have already been used in the cosmetics field. Their film-forming properties have been used to advantage in hair products, such as shampoos and gels, in order to facilitate hair form retention and hair shaping.

The present invention proposes to use a vinylpyrrolidone/vinyl acetate copolymer as perfume extender.

DESCRIPTION OF THE INVENTION

A subject of the present invention is thus a perfuming composition, said composition comprising:
from 40% to 90% by weight of ethanol,
from 0% to 30% by weight of water,
from 3% to 40% by weight of a perfume concentrate, and
from 1% to 10% by weight of a vinylpyrrolidone/vinyl acetate copolymer, which is preferably solid at 25° C.,
the percentages being expressed relative to the weight of the composition.

The perfuming composition may consist of:
from 40% to 90% by weight of ethanol,
from 0% to 30% by weight of water,
from 3% to 40% by weight of a perfume concentrate, and
from 1% to 10% by weight of a vinylpyrrolidone/vinyl acetate copolymer, which is preferably solid at 25° C.,
the percentages being expressed relative to the weight of the composition.

The term "perfuming composition" or "perfume" is intended to mean a product in liquid form intended to impart a pleasant smell on an individual after it has been sprayed or applied to: the skin, the hair or the clothing of the individual. Such a product is not rinsed off after application. A perfume is generally applied to the skin.

The term "comprising" is intended to mean that the composition may contain other ingredients. It is preferred for the sum of the percentages of ethanol, water, perfume concentrate and copolymer to be greater than or equal to 95% by weight, more preferably greater than 98% by weight of the weight of the composition.

The term "consist of" is intended to mean that the sum of the percentages of ethanol, water, perfume concentrate and copolymer is equal to 100%.

The copolymer makes it possible to increase the persistence of the olfactory note of the composition without changing the original olfactory note perceived at the time of use. Incorporated into a perfuming solution, this copolymer does not significantly modify the capacity of the solution to be satisfactorily sprayed.

The composition is preferably a sprayable, transparent, non-tacky perfume formula which is stable over time and heat-stable. The olfactory note of the perfuming composition in its packaging does not significantly vary after exposure of said composition to heat for several weeks.

The term "sprayable" is intended to mean the ability of a composition to be sprayed in a manner that the consumer finds satisfactory, said consumer expecting it to be possible for said composition to be sprayed evenly and repeatedly while producing a result that is satisfactory in terms of uniformity of the size of the droplets formed upon spraying, at the surface formed by the cloud of composition sprayed at a given distance, or as the result obtained after application to the skin.

The copolymer does not significantly modify the olfactory note of an alcoholic solution of a perfume concentrate. It also makes it possible to preserve the original olfactory note under standard conditions of accelerated aging, in particular by exposure to heat.

Thus, the copolymer improves the properties of the perfuming compositions, in particular their persistence on the skin or the hair, while at the same time obtaining a transparent composition that can be sprayed, and the sensory properties of which, such as the feel, are satisfactory.

The copolymer advantageously extends the perception of the perfume over time, in particular the top notes and the heart notes of the perfume, for a user who has sprayed the composition onto their skin or their clothing, this increase being evaluated relative to the same composition not containing said copolymer.

In the copolymer, the weight ratio of the vinylpyrrolidone to the vinyl acetate in the copolymer can advantageously range from 50:50 to 70:30. It is for example 60:40.

The weight-average molecular weight of the copolymer, measured according to the small angle laser diffraction method, is preferably between 15 000 and 600 000, more preferably between 30 000 and 100 000. The weight-average molecular weight of the copolymer is for example about from 40 000 to 50 000.

The copolymer is preferably solid at 25° C., and can be in the form of a powder. The INCI name of the copolymer may be VP/VA Copolymer. It preferably has a glass transition temperature of between 70 and 115° C., more preferably between 100 and 110° C.

The composition is liquid at 25° C., and is advantageously in the form of a solution of the ingredients of which it is composed. It may be aqueous-alcoholic or alcoholic. The term "aqueous-alcoholic composition" is intended to mean a composition containing ethanol or water, and the term "alcoholic composition" is intended to mean a composition containing ethanol and not containing water. The ethanol used for the formulation of the compositions is generally 96 vol % ethanol (i.e. containing 4% of water). For the purposes of the present invention, when the percentage of water in the composition is expressed, this is intended to mean the percentage of water that the composition contains i) due to the use of 96 vol % ethanol, or ii) due to the addition of water to absolute ethanol. In the context of the invention, the expression "from . . . to" is intended to include the limits of the range of values, unlike the expression "between . . . and" which is intended to exclude the limits of the range of values.

The composition is advantageously in the form of a solution in which the ingredients are miscible. In this case, the composition is not in the form of a water-in-oil or oil-in-water emulsion.

The composition advantageously contains from 0% to 0.01% by weight of surfactant. It is preferably free of surfactant. Indeed, the copolymer is soluble at the same time in ethanol, the perfume concentrate, and the mixture of the two, so that it is not necessary to add a surfactant for the composition to be homogeneous and transparent.

The composition may in particular be free of polyoxyalkylenated surfactants comprising at least five units chosen from —$CH_2CH(OH)CH_2$— and —$OCH_2CH_2$—, such as polyoxyethylenated compounds and polyoxypropylenated compounds. Among these surfactants, mention may be made of polyoxyalkylenated ethers, for instance POE(10) cetyl ether, polyoxyalkylenated esters, for instance PEG-40 hydrogenated castor oil or POE(20) sorbitan monolaurate, polyoxyethylenated alkylphenol condensates, products of condensation of ethylene oxide with the product of reacting propylene oxide and ethylenediamine, polyethoxylated alcohols, polysorbates, and dimethicone copolyols.

The copolymer is advantageously in an amount sufficient to increase the persistence of the perfume concentrate over time, once the composition has been applied to the skin or the hair, without reducing the transparency and the sprayability of the composition.

In one embodiment, the copolymer represents from 1% to 10% by weight of the composition. Above 10% by weight, the copolymer has a negative effect: it produces a tacky sensation on the skin and it prevents good spraying of the composition. In one embodiment, the copolymer represents from 2% to 8%, preferably from 2% to 5% by weight of the weight of the composition.

The minimum concentration of copolymer has a value chosen from the group consisting of 1%, 2% and 3% by weight of the weight of the composition. The maximum concentration of copolymer has a value chosen from the group consisting of 4%, 5%, 6%, 7%, 8%, 9% and 10% by weight of the weight of the composition.

The composition contains a perfume concentrate. The perfume concentrate may be for example chosen from compounds of which the INCI name appearing on the list of ingredients of the perfuming composition proposed for sale is "Perfume". A perfume concentrate is a compound or a mixture of compounds that is at least partially volatile at ambient temperature, and the odor of which is detected. The perfume concentrate contains a note chosen from the group consisting of the top notes, the heart notes, the base notes, and mixtures thereof. The perfume concentrate preferably comprises predominantly top notes and heart notes, and corresponds to low-persistence or medium-persistence perfumes.

The term "low-persistence" or "medium-persistence" is intended to mean a perfume for which the odor perception, observed by an experienced panel, decreases by more than half after 8 hours following application to the skin.

The perfume concentrate is prepared from natural or synthetic perfuming materials.

As perfuming materials of natural origin, mention may be made for example of extracts of flowers (lavender, rose, jasmine, ylang-ylang), of stems and of leaves (patchouli, geranium, petitgrain), of fruits (coriander, aniseed, cumin, juniper), of fruit peels (bergamot, lemon, orange), of roots (angelica, celery, cardamom, iris, sweet flag), of wood (sandalwood, guaiacum, Spanish cedar), of grasses and graminae (tarragon, lemongrass, sage, thyme), of resins and of balms (galbanum, elemi, benzoin, myrrh, olibanum, opopanax).

As perfuming materials of synthetic origin, mention may be made for example of benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbinyl acetate, phenylethyl acetate, linalyl benzoate, benzyl formate, ethyl methyl phenyl glycinate, alkylcyclohexyl propionate, styralyl propionate and benzyl salicylate, benzylethyl ether, linear alkanals containing from 8 to 18 carbon atoms, citral, citronellal, citronellyloxyacetaldehyde, cyclamen aldehyde, hydroxycitronellal, lilial and bourgeonal, ionones such as alpha-isomethylionone, and methyl cedryl ketone, anethol, citronellol, eugenol, isoeugenol, geraniol, linalool, phenylethyl alcohol, terpineol, and terpenes. These compounds are often in the form of a mixture of two or more of these odorous substances.

Moreover, use may also be made of essential oils, for instance essential oils of sage, chamomile, clove, melissa balm, mint, cinnamon tree leaves, juniper, vetiver, oliban, galbanum, labdanum and lavandin.

Use is preferably made, as perfume, alone or as a mixture, of essential oil of bergamot, dihydromyrcenol, lilial, lyral, citronellol, phenylethyl alcohol, alpha-hexylcinnamaldehyde, geraniol, benzylacetone, cyclamen aldehyde, linalool, ambroxan, indole, hedione, sandelice, essential oils of lemon, of mandarin and of orange, allylamine glycolate, cyclovertal, essential oil of lavandin, essential oil of sage, beta-damascone, essential oil of geranium, cyclohexyl salicylate, phenylacetic acid, geranyl acetate, benzyl acetate, and rose oxide.

Among the known olfactory notes, mention may be made for example of hesperide perfumes, aromatics, floral perfumes, musks, fruity perfumes, spicy perfumes, oriental perfumes, marine perfumes, aquatic notes, chypre perfumes, woody perfumes, ferns and mixtures thereof.

The ethanol content in the composition can range from 40% to 90% by weight, preferably from 50% to 85% by weight relative to the weight of the composition.

In a first embodiment, the composition contains from 15% to 25% by weight of perfume concentrate, from 55% to 65% by weight of ethanol and from 15% to 25% by weight of water relative to the weight of the composition.

In a second embodiment, the composition contains from 25% to 35% of perfume concentrate, from 70% to 80% by weight of ethanol and 0% by weight of added water relative to the weight of the composition.

In a third embodiment, the composition contains from 15% to 25% by weight of perfume concentrate, from 75% to 85% by weight of ethanol and from 0% to 5% by weight of water relative to the weight of the composition.

Generally, when the composition contains water, the weight ratio of ethanol to water is between 65/35 and 98/2, preferably between 70/30 and 85/15, and more preferably between 75/25 and 80/20 in the composition of the invention.

The perfume concentrate can represent from 6% to 30% by weight of the composition, for example from 6% to 15%, or from 10% to 25%, or else from 20% to 30% by weight of the weight of the composition. The perfume concentrate can represent from 3% to 40%, for example from 10% to 35% or from 15% to 30% by weight of the weight of the composition.

The composition may contain, in addition to the ingredients previously described, at least one cosmetically acceptable ingredient chosen from dyes, UV-screening agents, cosmetic active agents, antioxidants and refreshing agents.

The dyes are for example: caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, cochenille carmine (Cl 15850, Cl 75470), Ext. Violet 2, Red 6-7, Ferric Ferrocyanide, Ultramarines, Acid Yellow 3/Yellow 10, Acid Blue 3, Yellow 10. The liposoluble dyes are for example Soudan red, D&C Red 17, D&C Green 6, beta-carotene, soybean oil, Soudan brown, D&C Yellow 11, D&C Violet 2, D&C Orange 5, quinoline yellow and annatto.

The dyes generally represent from 0.01% to 1%, preferably from 0.05% to 0.5%, by weight of the weight of the perfuming composition.

Among the antioxidants, mention may be made for example of ascorbic acid, di-tert-butyl-p-hydroxytoluene (also called BHT or 2,6-di-tert-butyl-p-cresol), BHA (tert-butyl-4-hydroxyanisole), tocopherols such as vitamin E, tocopherol derivatives such as tocopheryl acetate, and gallic acid and its derivatives.

The composition may also comprise one or more agents which modify the evaporation curves of the molecules present in the perfume concentrate. Such modifiers are chosen from glycols, in particular from optionally hydroxylated or polyalkylenated ethers, $C_4$ to $C_{12}$ glyceryl ethers, esters, and polyalkylenated esters.

One of these ethers can correspond to a compound of formula R—O—(CH(CH$_3$)—CH$_2$O)$_a$—(CH$_2$—CH$_2$O)$_b$—H in which a and b are integers such that the sum of a and b ranges from 1 to 4, and R is an aliphatic chain comprising from 8 to 18 carbon atoms.

An ether can for example be chosen from polyoxyethylene glyceryl monococoate (Cetiol® HE), dicaprylyl ether (Cetiol® OE), PPG-11 stearyl ether (Arlamol® E), PPG-3 myristyl ether (Tegosoft® APM), and mixtures thereof.

Glyceryl ethers may be in accordance with those described in document U.S. 2003/0216283, in particular 2-ethylhexyloxypropanediol.

An ester may be n-hexadecyl-n-nonanoate, n-octadecyl-n-nonanoate or neopentyl glycol diisononanoate.

A subject of the invention is also a bottle equipped with a spraying means and with a packaging means, and containing the composition described above.

The spraying means may be a manual pump. The bottle is preferably transparent in order to allow the composition of the invention to be observed, said composition itself preferably being transparent.

The compositions can be applied in the form of fine droplets by means of pressurization devices. These devices are well known to those skilled in the art and comprise non-aerosol pumps or "atomizers", aerosol containers comprising a propellant and also aerosol pumps using compressed air as propellant.

The compositions and the bottles of the invention can be in the form of eau de toilette, eau de cologne, perfume extract, esprit de parfum or eau de parfum.

Another subject of the invention is a method for perfuming the skin or the hair of an individual, which consists in applying, using a spraying means, to the skin or the hair of the individual, the composition described above. The composition may also be applied to clothing also; it is preferably applied directly to the skin, preferably to a part of the body which is not the face.

A further subject of the invention is the use of a vinylpyrrolidone/vinyl acetate copolymer in a perfuming composition, for extending the time during which the olfactory note of said composition is perceived by the sense of smell of a user having applied it to a support, this increase being evaluated relative to the same composition not containing said copolymer. The support on which the perfume is deposited may be for example the skin of an individual or a mineral or organic, preferably porous, support. The composition is preferably a perfuming solution in the form of eau de toilette, eau de cologne, perfume extract, esprit de parfum or eau de parfum, applied to the skin, the hair or the clothing.

The copolymer advantageously extends the perception of the top notes and of the heart notes of the olfactory note.

A subject of the present invention is also a diffuser comprising a support impregnated with the perfuming composition described above. The support may be mineral or organic, and preferably porous.

The support on which the perfume of the invention can be deposited is for example a fabric or a ceramic. The ceramics may be produced according to the techniques known to those skilled in the art. The fabrics may be wipes used in the field of perfuming or perfumed products, or felts.

The diffuser may be obtained by impregnating the support with the perfuming composition by any means known to those skilled in the art. The impregnation can thus be carried out i) by capillary action after the composition has been either poured dropwise or sprayed onto the support, or ii) by dipping the support in a container containing the perfuming composition.

The invention will be illustrated in greater detail by the following examples.

EXAMPLE 1 AND COMPARATIVE EXAMPLES

Evaluation of the Olfactory Fidelity and of the Persistence of a Perfuming Composition According to the Invention and of a Perfuming Composition of the Prior Art A commercial perfume of "floral" type of medium persistence was chosen as Reference.

A composition according to the invention, obtained by adding a VP/VA copolymer to the Reference was then prepared. The vinylpyrrolidone (VP)/vinyl acetate (VA) copolymer that was used has a maximum solubility, measured at 25° C., of 40% by weight of 96% v/v ethanol (comprising 4% v/v of water). The intrinsic olfactory neutrality of the copolymer was verified. Such a copolymer is for example sold under the reference PVP/VA S-630® by the company ISP.

By way of comparison, various polyvinylpyrrolidone (PVP) polymers were tested as a function of their physical characteristics (chain length and crosslinking), their chemical characteristics (hydrophilicity/lipophilicity) and their sensory properties (odor and color).

These polymers were introduced into the commercial perfume at a concentration previously defined as the maximum concentration at which the perfume is sprayable with a manual pump.

TABLE 1

Concentration of the copolymer in the reference

| Solutions | Polymer introduced into the Reference | PHYSICAL CHARACTERISTICS | Concentration of the copolymer in the Reference |
|---|---|---|---|
| Comparative solution 1 | PVP | MW: 2000000-3000000 | 0.5% |
| Comparative solution 2 | PVP | MW: 900000-1500000 | 2% |
| Comparative solution 3 | PVP | MW: 40000-80000 | 3% |
| Solution in accordance with the invention | VP/VA copolymer | MW: 30000-60000 VP/VA weight ratio = 60/40 | 4% |

MW: Weight-average molecular weight of the polymer

The olfactory fidelity of the Solutions was evaluated relative to the Reference by a sensory panel made up of eight individuals, immediately after application to the skin (T0)

and 8 hours after application (T0+8 hours), by following a precise spreading protocol. The score was given on a scale of 0 to 9, 9 representing the optimum fidelity. A similar protocol was used to determine the persistence of the Solutions at T0+8 hours, graded on a scale of 0 to 9, where 9 represents the most favorable note.

The members of the sensory panel were experts i) with experience of objective and descriptive characterizations of the sensory qualities of perfumed or perfuming cosmetic compositions, and ii) able to disregard the hedonic components with ease.

The experts of the panel were instructed as to how to assign grades and judge the differences. In addition, the experts had to not wear perfume nor apply a perfumed cream on the days of evaluation.

The protocol followed by each expert was the following:
The Solution is sprayed once without applying it in order to correctly prime the pump.
A single spray of the Solution is applied, at approximately 5 cm from the arm, to the skin of the top/middle upper part of the forearm of the expert, and the same application is carried out with the Reference on the other forearm.
The olfactory fidelity is evaluated at T0 on a scale of 0 to 9 by comparing the perfume notes of the Reference and of the Solution.
A plastic circle is applied around each of the two areas of perfumed skin in order to protect them against rubbing; they are attached with a band-aid and then a period of 8 hours is allowed to elapse.
At T0+8 hours, the two plastic circles are removed and, after 10 seconds, the perfumed areas are smelt at approximately 2 cm from the surface of the skin and the persistence or the olfactory fidelity of the Solution is evaluated on a scale of 0 to 9.

The results have been reported in tables 2 and 3 below.

TABLE 2

Olfactory fidelity at T0

| Solutions | PERCENTAGE | Fidelity T0 relative to the Reference |
|---|---|---|
| Comparative solution 1 | 0.5% PVP | 6.75 |
| Comparative solution 2 | 2% PVP | 7.1 |
| Comparative solution 3 | 3% PVP | 8 |
| Solution in accordance with the invention | 4% VP/VA copolymer | 8 |

TABLE 3

Fidelity and persistence at T0 + 8 hours

| INGREDIENTS | PERCENTAGE of polymer | Persistence T0 + 8 H | Fidelity T0 + 8 H |
|---|---|---|---|
| Reference | 0% | 5 | — |
| Comparative solution 1 | 0.5% PVP | 5.4 | 6.4 |
| Comparative solution 2 | 2% PVP | 6.2 | 6.6 |
| Comparative solution 3 | 3% PVP | 4.8 | 7.5 |
| Solution of the invention | 4% VP/VA copolymer | 6.4 | 7.5 |

This study indicates that only the VP/VA copolymer makes it possible to significantly improve both the olfactory fidelity and the persistence of the perfume, without any impact on its physical and sensory properties.

The fidelity of the olfactory note is respected, the sprayability is preserved, and a good compromise can be obtained between the sensoriality and the duration of the product after application.

EXAMPLE 2

Increase in the Persistence of Various Perfumes

A study similar to that of example 1 was carried out by dissolving a VP/VA copolymer at 4% by weight in accordance with that used in example 1, respectively in four commercial perfumes P1 to P4 having different persistences (see Table 4). The results have been presented in Table 5.

TABLE 4

Persistence of the Reference perfumes

| Reference perfume without polymer | Persistence T0 + 8 H of the perfume without polymer |
|---|---|
| P1 | 3 |
| P2 | 4 |
| P3 | 5 |
| P4 | 6 |

TABLE 5

Olfactory fidelity and persistence of the solutions of the invention

| Perfume containing the VP/VA copolymer | Olfactory fidelity T0 + 8 H | Persistence T0 + 8 H | Increase in persistence T0 + 8 H |
|---|---|---|---|
| P1 with 4% of VP/VA | 7.2 | 5.8 | 93% |
| P2 with 4% of VP/VA | 7.3 | 5.8 | 45% |
| P3 with 4% of VP/VA | 7.5 | 6.4 | 28% |
| P4 with 4% of VP/VA | 6.8 | 6.7 | 12% |

The increase in the persistence at T0+8H is significant when a VP/VA copolymer dissolved at 4% by weight is added to the perfume, whatever the olfactory family of the perfume.

The most significant effect was obtained with a very light perfume of which the persistence was about 3 to 4.

EXAMPLE 3

Preparation of Ceramics Impregnated with the Perfuming Composition of the Invention and Comparison with Respect to an Impregnation with a Perfuming Composition of the Prior Art Ceramic impregnation tests were carried out with the perfume P1 and the Reference perfume without polymer, these two perfumes being in accordance with those described in example 2.

The "Control" diffuser consists of a ceramic that has been impregnated by dipping, by completely immersing it for 30 seconds, at 25° C., in the Reference perfume, the Reference perfume illustrating the prior art and being free of PVP-VA copolymer.

The diffuser of the invention consists of a ceramic having the same characteristics as the ceramic of the control diffuser, previously used, and which was perfumed by dipping in the perfume P1 in accordance with the invention containing the PVP/VA copolymer, under the same dipping conditions as those used to prepare the control ceramic.

A grade of between 0 and 4 (4 being the maximum grade of persistence observed) is assigned by an olfactory panel in accordance with that used in Example 1. This grade characterizes the persistence of the perfume P1 or of the Reference perfume on ceramic.

Three grades were assigned:
to the ceramic that has been dipped and that has thus been taken out of the beaker, without subsequent drying (grade at T0)
to the ceramic in accordance with T0 that has subsequently been stored for 6 months at ambient temperature (grade at T1), then
to the ceramic in accordance with T1 that has subsequently been subjected to accelerated aging for 3 weeks in an oven at 45° C. (grade at T2).

The average grades assigned are reported in the following table.

|  | T0 | T1 = T0 + 6 months ambient temperature | T2 = T1 + 3 weeks at 45° C. |
| --- | --- | --- | --- |
| Control diffuser | 4 | 2 | 3.5 |
| Diffuser of the invention | 4 | 1.5 | 3 |

The invention claimed is:
1. A bottle comprising:
a container;
a sprayer; and
in the container a sprayable liquid perfuming composition in a form of eau de toilette, eau de cologne, perfume extract, esprit de parfum or eau de parfum, comprising:
from 40% to 90% by weight of ethanol,
from 0% to 30% by weight of water,
from 10% to 35% by weight of a perfume concentrate, and
from 2% to 5% by weight of a vinylpyrrolidone/vinyl acetate copolymer,
the percentages being expressed relative to the weight of the composition,
wherein a weight ratio of the vinylpyrrolidone to the vinyl acetate in the copolymer is 60:40.

2. The bottle as claimed in claim 1, wherein the copolymer provides an extension of a time period during which top notes and heart notes of the composition are perceived by the sense of smell of a user when the user sprays the composition onto skin or clothing, said extension of the time period being evaluated relative to a similar composition not containing said copolymer.

3. The bottle as claimed in claim 1, wherein the copolymer is solid at 25° C., and has a weight-average molecular weight between 15,000 and 600,000.

4. The bottle as claimed in claim 1, wherein the weight ratio of ethanol to water is between 65/35 and 98/2.

5. The bottle as claimed in claim 1, wherein the composition contains from 15% to 25% by weight of perfume concentrate, from 55% to 65% by weight of ethanol and from 15% to 25% by weight of water relative to the weight of the composition.

6. The bottle as claimed in claim 1, wherein the composition contains from 25% to 35% of perfume concentrate, from 70% to 80% by weight of ethanol and 0% by weight of water relative to the weight of the composition.

7. The bottle as claimed in claim 1, wherein the composition contains from 15% to 25% by weight of perfume concentrate, from 75% to 85% by weight of ethanol and from 0% to 5% by weight of water relative to the weight of the composition.

8. The bottle as claimed in claim 1, wherein the composition is transparent.

9. The bottle as claimed in claim 1, wherein the sprayer comprises a manual pump.

* * * * *